United States Patent
Lam et al.

(10) Patent No.: US 6,733,530 B1
(45) Date of Patent: May 11, 2004

(54) MATERIAL AND METHOD FOR ENGRAFTMENT OF A COMPOSITE BIOCOMPATIBLE SKIN GRAFT ON THE NEODERMIS OF ARTIFICIAL SKIN

(75) Inventors: Ping Kuen Lam, 1B, Linden Height, 11 Boyce Rd., Jardine's Lookout, SAR (HK); Eric Sun-Yin Chan, 11B, Kingston Heights, Belair Gardens, Shatin, N.T. (HK)

(73) Assignees: Eric Sun-Yin Chan, San Jose, CA (US); Ping Kuen Lam (CN)

( * ) Notice: Subject to any disclaimer, the term of this patent is extended or adjusted under 35 U.S.C. 154(b) by 0 days.

(21) Appl. No.: 09/365,677

(22) Filed: Aug. 2, 1999

(51) Int. Cl.[7] .............................. A61F 2/00; A61F 2/02; A61F 2/10; A61F 13/00
(52) U.S. Cl. .................... 623/15.12; 424/422; 424/425; 623/11.11; 623/15.11
(58) Field of Search ........................... 623/11.11, 15.11, 623/15.12; 424/422, 425

(56) References Cited

U.S. PATENT DOCUMENTS 5,489,304 A * 2/1996 Orgill et al. .................. 623/15
5,658,331 A * 8/1997 Della Valle et al. .......... 623/15

OTHER PUBLICATIONS

Hansbrough et al. (1989) Burn wound closure with cultured autologous keratinocytes and fibroblasts attached to a collagen–glycosaminoglycan substrate. JAMA 262(15): 2125–2130.*
Cooper et al. (1993) Direct comparison of a cultured composite skin substitute containing human keratinocytes and fibroblasts to an epidermal sheet graft containing human keratinocytes on athymic mice. J. Invest. Dermatol. 101: 811–819.*
Myers et al. (1997) A hyaluronic acid membrane delivery system for cultured keratinocytes: Clinical "take" rates in the porcine kerato–dermal model. J. Burn Care Rehabil. 18: 214–222.*
Rennekampff et al. (1996) Wound closure with human keratinocytes cultured on a polyurethane dressing overlaid on a cultured human dermal replacement. Surgery 120: 16–22.*
Zacchi et al. (1998) In vitro engineering of human skin–like tissue. J. Biomedical Materials Research 40:187–194.*
P A Harris, et al., "Use of hyaluronic acid and cultured autologous keratinocytes and fibroblasts in extensive burns," *The Lancet*, vol. 353, pp. 35–36 (Jan. 2, 1999).
Howard Green, et al., "Growth of cultured human epidermal cells into multiple epithelial suitable for grafting," *Proc. Natl. Acad. Sci. USA*, vol. 76, No. 11, pp. 5665–5668, (Nov. 1979).
George J. Todaro, et al., "Antigenic and Cultural Properties of Cells Doubly Transformed by Polyoma Virus and SV40," *Virology*, vol. 27, pp. 179–185, (1995).
Rheinwald et al., *Cell*, 6:331–344 (1975).
Tompkins et al., *World J Surgery*, 16:47–52 (1992).
Herzog et al., *J Trauma*, 28:195–1999 (1991).
Yannas et al., *Science*, 215:174–176 (1982).
Heimbach et al., *Ann Surgery*, 208:313–320 (1988).
Sheridan et al., *Eur J Plast Surgery*, 17:91–93 (1994).
Sheridan et al., *Burns*, 25:97–103 (1999).
Pandya et al., *Plast Reconst Surgery*, 102:825–828 (1998).
Hultman et al., *J Trauma*, 41:51–60 (1996).
Lam et al., *Abstracts of the 10th Congress of International Society For Burn Injuries*, Jerusalem, Israel, p. 46 (Nov. 1–6, 1998).
Sato et al., *J Investigative Dermatology*, 109:334–339 (1997).
Panos et al., *J Clin Invest*, 92:969–977 (1993).
Burd et al., *Br J Plast Surgery*, 44:579–584 (1991).
Feinberg et al., *Science*, 220:1177–1179 (1983).
Altman, *Practical Statistics for Medical Research*, 211:260–261 (1991).
Job et al., *Lancet*, 353:35–36 (1999).
Myers et al., *J Burn Care Rehabil*, 18:214:222 (1997).
Hansbrough et al., *J Burn Care Rehabil*, 13:519–529 (1992).
Chan et al., *Plast. Reconstr. Surg.*, 105:807–808 (2000).
Lam et al., *J Trauma*, 47:918–922 (1999).
Chan et al., *J Trauma*, 50:358–362 (2001).

* cited by examiner

*Primary Examiner*—Anne-Marie Falk
(74) *Attorney, Agent, or Firm*—Townsend and Townsend and Crew LLP (57) ABSTRACT

Autologous cultured keratinocytes are grown on a biosynthetic and biocompatible substratum following pre-seeding with autologous or allogenic dermal fibroblasts. The resultant composite material may then be applied on the neodermis of artificial skin which had been previously engrafted on the patient. The composite material, and specifically Composite Biocompatible Skin Graft (CBSG) material comprises autologous keratinocytes A and allogenic or autologous dermal fibroblasts grown on an artificial skin. A method for cultivating the CBSG includes the application of dermal fibroblasts onto the substratum as a feeder layer and then the inoculation of autologous keratinocytes on the resultant structure. A method for engraftment comprises first applying an artificial skin with a protective silicone membrane on a wound area, thereby allowing vascularization; and following vascularization, removing the silicone membrane and engrafting the CBSG material onto the vascularized artificial skin.

24 Claims, 5 Drawing Sheets

FIG. 8 grafted CBSG
wound bed

MATERIAL AND METHOD FOR ENGRAFTMENT OF A COMPOSITE BIOCOMPATIBLE SKIN GRAFT ON THE NEODERMIS OF ARTIFICIAL SKIN

REFERENCE TO SPONSORSHIP

This invention was made under the joint sponsorship of the Chinese University of Hong Kong of Shatin, Hong Kong SAR, and the Hospital Authority, also known as the Prince of Wales Hospital of Shatin, Hong Kong SAR.

BACKGROUND OF THE INVENTION

This invention relates to the cultivation of keratinocytes and dermal fibroblasts on a biosynthetic membrane and subsequent engraftment of this type of membrane on the neodermis of artificial skin with particular application to humans. This invention also relates to fabricated graft materials.

Prompt wound coverage for protection and stabilization is essential for the treatment of burns. The 3T3 cell-feeder layer technique developed by Rheinwald and Green in the 1970s is the standard method for cultivation of autologous epidermal autograft or so-called cultivated epidermal autograft material ("CEA"). A small piece of native skin from the patient can be cultured and expanded to 500 times or more in size within 3–4 weeks. However, the lack of dermis and the fragility of the cultured graft often result in unpredictable grafting success rates ranging from 0%–80%, as reported by Tompkins et al. (1992) and Herzog et al. (1991).

ALLODERM™ and INTEGRA™ human skin substitutes are two currently popular examples of human skin substitute commercially available in the market. INTEGRA™ artificial skin, a brand of artificial skin is sold by Integra LifeScience Corporation of New Jersey, USA, and has been approved by FDA for use in the USA since 1996. Artificial skin is a bilayer biosynthetic sheet comprising porous collagen-glycoaminoglycan integrated with a thin silicone membrane as an outer layer. The use of artificial skin such as INTEGRA™ artificial skin as a biocompatible a cellular dermal replacement in deep and full-thickness burn wounds is well known.

It has been observed that within about 14 to 21 days following the grafting of INTEGRA™ artificial skin, there is full vascularization of the neodermis formed in the INTEGRA™ artificial skin. Thereafter an ultra thin split thickness skin graft must be harvested from a donor site in order to cover the neodermis immediately after the silicone membrane is removed. Substantial research effort has been undertaken in the past to determine the possibility of reliably grafting CEA on the neodermis, since an effective combination of CEA and INTEGRA™ artificial skin should eliminate the second operative stage, the associated pain and scaring, as well as a need for a second donor site, which may not be available in extensively burned patients. If the grafted CEA does not 'take' on the neodermis of INTEGRA™ artificial skin after the silicone membrane is peeled off, it can be replaced by another CEA. Whereas, in the conventional application of INTEGRA™ artificial skin, another split thickness autograft must be harvested from a second or even a third donor site. There have been very limited initial anecdotal reports on experience with such a combination technique, such as Sheridan et al. 1999 and Pandya et al. 1998. At the 10th Congress of International Society For Burn Injuries, November 1998 in Israel, the difficulties with the conventionally cultured graft anchoring onto the neodermis of INTEGRA™ artificial skin were addressed. The exact reasons for such difficulties remain unknown.

LASERSKIN™ artificial skin material is a thin and pliable biosynthetic membrane comprising a 100% benzyl esterified hyaluronic acid derivative suitable for use as a substratum in the growth of skin cells. The recommendation of the manufacturer is to seed human keratinocytes on LASERSKIN™ artificial skin preseeded with irradiated 3T3 cells as feeder layer. When following the manufacturer's recommendation, it was found that, after the initiation of the formation of keratinocyte colonies, the xenogenic 3T3 cells growing on the LASERSKIN™ artificial skin were less likely to be washed away than those growing on a culture dish as in the conventional Green's method during each flushing procedure with phosphate-buffered saline. It is believed that the remaining 3T3 cells or debris might have sensitized the host to xenogenic antigen resulting in undesired late graft rejection. What is needed is a cultivation and engraftment procedure with a biocompatible, durable human skin substitute.

Related References

The following references, not all of which are prior art for the purposes of a patent application, are hereby made of record and incorporated herein by reference for the purposes described in this text:

1) Rheinwald J, Green H. "Serial cultivation of strain of human epidermal keratinocytes: The formation of keratinizing colonies from single cells." Cell 1975; 6: 331–344.
2) Tompkins R G, Burke J F. "Burn wound closure using permanent skin replacement material." World J Surgery 1992; 16: 47–52.
3) Herzog S R, Meyer A, Woodley D, Peterson H D. "Wound coverage with cultured autologous keratinocytes: Use after burn wound excision, including biopsy follow-up." J Trauma 1991; 28: 195–1999.
4) Yannas I V, Burke J F, Orgill D P, Skrabut E M. "Wound tissues can utilize a polymeric template to synthesize a functional extension of skin." Science 1982; 215: 174–176.
5) Heimbach D, Letterman A, Burke J et al. "Artificial dermis for major burns. A multi-center randomized clinical trial." Ann Surgery 1988; 208: 313–320.
6) Sheridan R L, Heggerty M, Tompkins R G, Burke J F. "Artificial skin in massive burns-results at ten years." Eur J Plast Surgery 1994; 17: 91–93.
7) Sheridan R L, Tompkins R G. "Skin substitutes in burns." Burns 1999; 25: 97–103.
8) Pandya A N, Woodward B, Parkhouse N. "The use of cultured autologous keratinocytes with Integra in the resurfacing of acute burns." Plast Reconst Surgery 1998; 102: 825–828.
9) Hultman C S, Brinson G M, Silitharm S, et al. "Allogenic fibroblasts used to grow cultured epidermal autografts persist in vivo and sensitize the graft recipient for accelerated second-set rejection." J Trauma 1996; 41: 51–60.
10) Lam P K, King W K, et al. "Development and evaluation of a new composite Laserskin graft" Abstracts of the 10th Congress of International Society For Burn Injuries, Nov. 1–6 1998, Jerusalem, Israel, p. 46.
11) Sato T, Kirimura Y, Mori Y. "The co-culture of dermal fibroblasts with human epidermal keratinocytes induces increased prostaglandin E2 production and cyclooxygenase 2 activity in fibroblasts." J Investigative Dermatology 1997; 109: 334–339.

12) Pano R J, Rubin J R, Aaronson S A, Mason R. "Keratinocytes growth factor and hepatocyte growth factor/scatter factor are heparin-binding growth factors for alveolar type II cells in fibroblast-conditioned medium."J Clin Invest 1993; 92: 969–977.
13) Burd DAR, Greco R M, Regauer M T, et al. "Hyaluron and wound healing: a new perspective." Br J Plast Surgery 1991; 44: 579–584.
14) Feinberg R N, Beebe D C. "Hyaluronate in vasoculogenesis." Science 1983; 220: 1177–1179.
15) Alman D G. Practical Statistics for Medical Research Chapman & Hall, London 1991 pp. 211, 260–261.
16) Harris P A, Francesco F di, Barisoni D, Leigh I M, Navsaria H A. "Use of hyaluronic acid and cultured autologous keratinocytes and fibroblasts in extensive burns." Lancet 1999; 353: 35–36.
17) Myers S R, Grady J, Soranzo C, Sander R, et al. "A hyaluronic acid membrane delivery system for cultured keratinocytes: Clinical take rates in the porcine Kerato-Dermal model." J Burn Care Rehabil 1977; 18: 214–222.
18) Hansbrough J F, Dore C, Hansbrough W N. "Clinical trials of living dermal tissue replacement placed beneath meshed, split-thickness skin grafts on excised burn wounds." J Burn Care Rehabil 1992; 13: 519–529.

SUMMARY OF THE INVENTION

According to the invention, autologous cultured keratinocytes grown on a biocompatible substratum are engrafted on the neodermis of artificial skin covering a wound. Autologous keratinocytes may be cultivated on a commercially available membrane such as LASERSKIN™ artificial skin (available from Fidia Advanced Biopolymers Ltd., Abano Terme (PD), Italy) following pre-seeding with autologous or allogenic dermal fibroblasts. The resultant composite material may then be applied on the neodermis of artificial skin which had been previously engrafted on the patient. The composite material, and specifically Composite Biocompatible Skin Graft (CBSG) material comprises autologous keratinocytes and allogenic or autologous dermal fibroblasts grown on the substratum. A method for fabricating the composite material includes the application of dermal fibroblasts onto the substratum as a feeder layer and then inoculating autologous keratinocytes on the resultant structure. A method for engraftment comprises first applying an artificial skin with a protective silicone membrane on a wound area, thereby allowing vascularization; following vascularization, removing the silicone membrane and engrafting the cultured composite material onto the vascularized artificial skin.

Human fibroblasts used in the cultivation technique according to the invention were found to achieve a role similar to 3T3 cells in the initiation of keratinocyte colonies on LASERSKIN™ artificial skin. Specifically, it was found that the seeding efficacy of human keratinocytes was increased to up to 95%. CBSG containing autologous keratinocytes and autologous dermal fibroblast or allogenic dermal fibroblasts or a combination of autologous and allogenic dermal fibroblasts according to the invention, has been successfully applied to burn patients whose wounds were previously grafted with allografts.

The purpose of this invention is to simplify burn treatment further and eventually to save lives of patients having extensive burns where little or no autologous skin grafts can be repeatedly harvested in a short period of time. With the inventive technique, all dead skin tissue of a patient with extensive burns can be excised within about three to seven days after injury. The wound can be covered with artificial skin, such as Integra™ or any dermal equivalent thereof, and only a small quantity of harvested normal skin would be required to initiate skin culture, which may thereafter be engrafted, according to the invention, on the neodermis of the artificial skin, with resultant lower rejection and infection incidences.

CBSG material according to the invention offers notable advantages. First, the basal proteins (including the early basement membrane proteins such as collagen IV and fibronectin) of the cultured graft are protected from dispase treatment because the keratinocytes are directly cultivated on a pliable LASERSKIN™ artificial skin. This is believed to enhance anchorage of the cultured keratinocytes on the neodermis of INTEGRA™ artificial skin. Second, in addition to acting as a feeder layer, the dermal fibroblasts in the inventive CBSG material evidently produce a number of proteins such as native collagen fibers and fibronectin which is believed to facilitate the attachment of a cultured graft. Third, the cultured keratinocytes of the inventive CBSG can be grafted five to seven days sooner than can traditionally-cultured keratinocytes. This is because cultured keratinocytes of the inventive CBSG are capable of being transferred and grafted at the sub-confluent or less differentiated stage rather than at a later confluent stage. Fourth, since there is minimal need for a donor site there is less likelihood of widespread scarring related to donor site harvesting. Fifth, the cultured keratinocytes of CBSG can be handled much more easily than the conventional CEA during its application on the neodermis of the artificial skin. Fewer cultured cells are lost or damaged during the transfer and application of CBSG. This should improve the success rate of the cultured graft. Sixth, the inventive engraftment technique can result in higher demand and broader scope of clinical applications for artificial skin.

The invention will be better understood by reference to the following detailed description in connection with the accompanying drawings.

DESCRIPTION OF THE SPECIFIC EMBODIMENTS

Figure 1A:
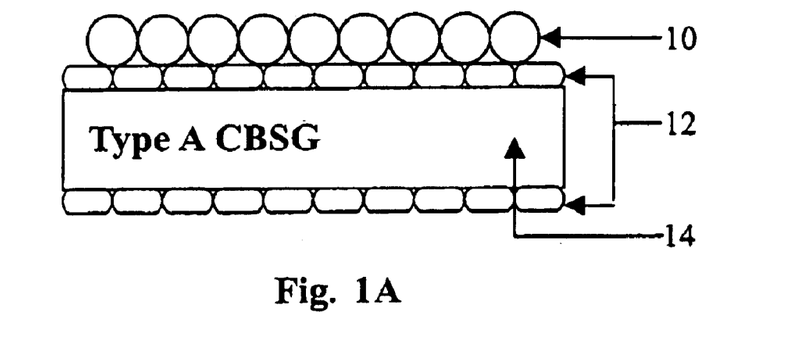
FIGS. 1A–1C are schematic diagrams of cross-sections of Type A, B and C embodiments of a cultured graft material according to the invention.

FIG. 1A, is what is herein termed a Type A composite skin graft material. In a specific embodiment it is formed by cultivating autologous keratinocytes on a commercially-available biosynthetic substratum 14 of a derivative of benzyl esterified hyaluronic acid. On the basal side and on the upper side of the substratum 14 layers of dermal fibroblasts 12 are seeded and grown. Over the dermal fibroblasts 12 of the upper side, a layer of autologous keratinocytes 10 is grown. The keratinocytes 10 are harvested from the target donor patient. The dermal fibroblasts can be autologous or allogenic.

Figure 1B:
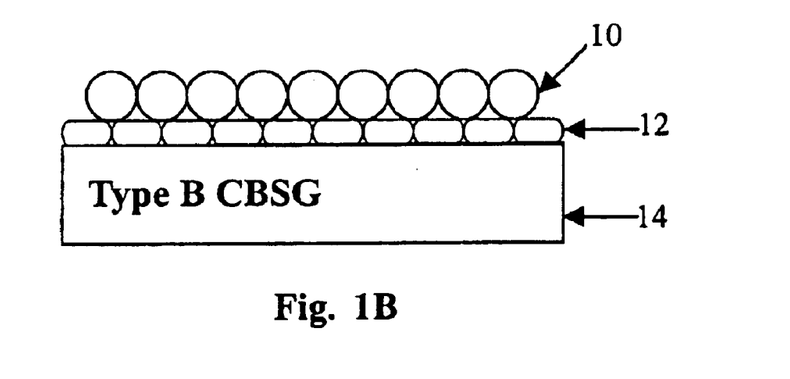

FIG. 1B is a Type B composite skin graft material. In a specific embodiment it is formed of a cultivation of autologous keratinocytes on commercially-available biosynthetic substratum 14. On the upper side of the substratum 14 there is a layer of dermal fibroblasts 12. Over the dermal fibroblasts 12 of the upper side is a layer of autologous keratinocytes 10. The dermal fibroblasts can be autologous or allogenic.

Figure 1C:
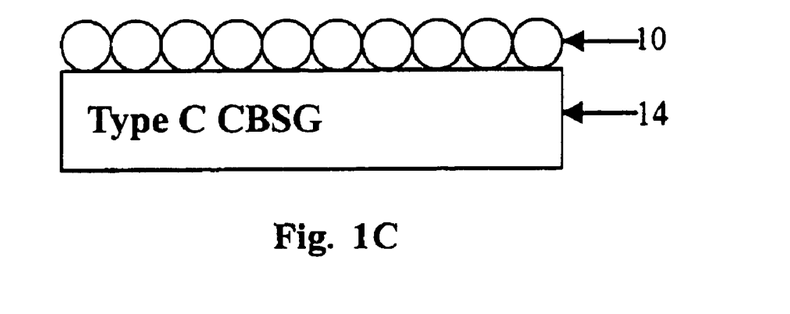

FIG. 1C is a Type C composite skin graft material. Originally intended as a control, it is, in a specific embodiment, formed of a cultivation of autologous keratinocytes on substratum 14. On the upper side of the substratum 14 there is merely a layer of keratinocytes 10.

Figure 2A:
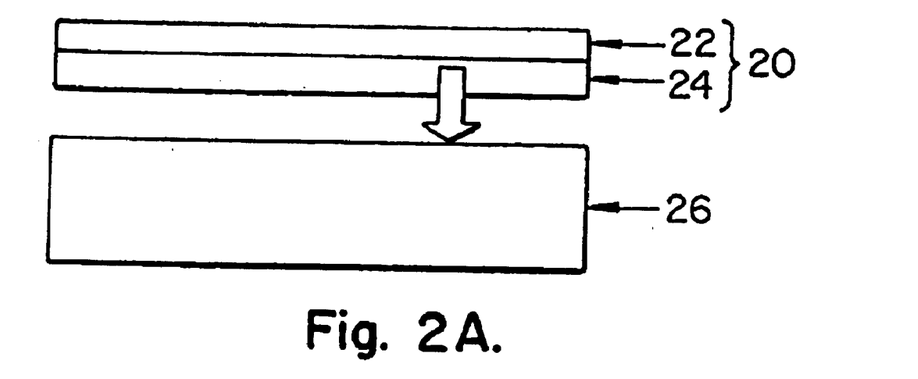
FIGS. 2A–2C are schematic diagrams of cross-sections of skin grafts illustrating the engraftment technique according to the invention.
Figure 2B:
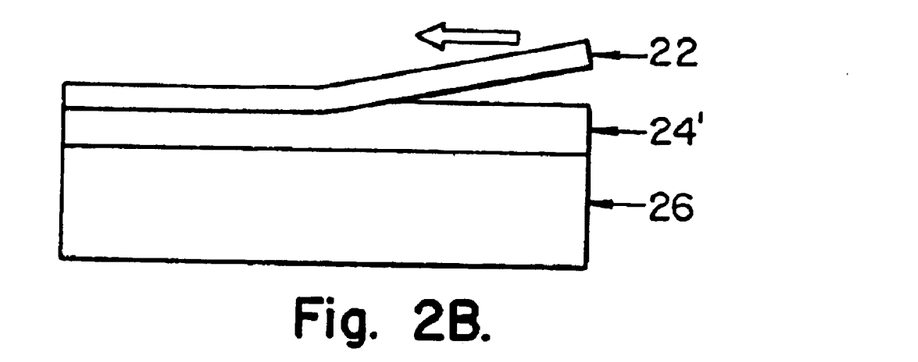
Figure 2C:
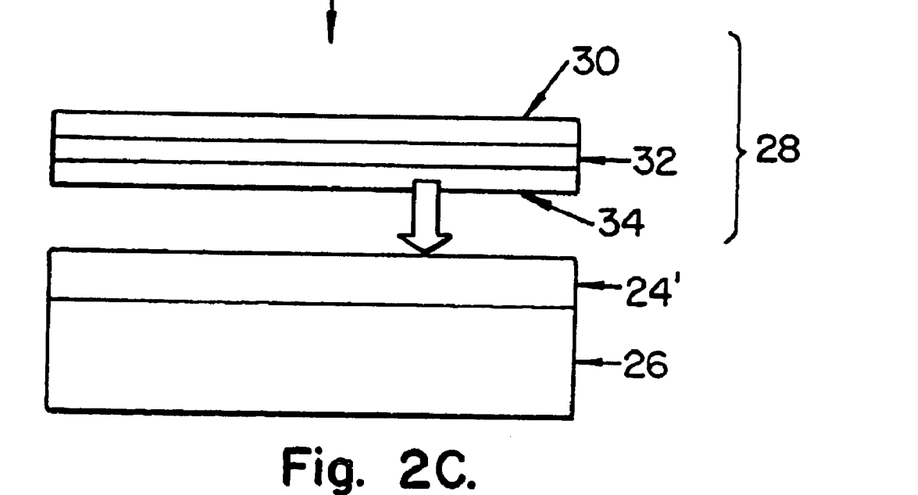
Figure 3:
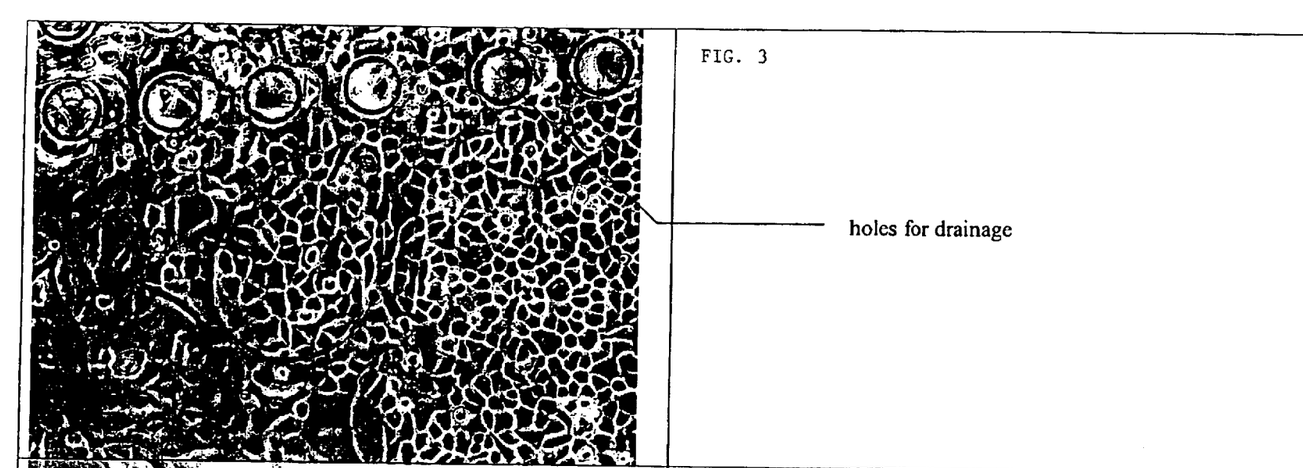
FIG. 3 is a photograph at 100×magnification depicting in vito proliferation of keratinocytes on plain LASERSKIN™ artificial skin showing holes for drainage of exudates.
Figure 4:
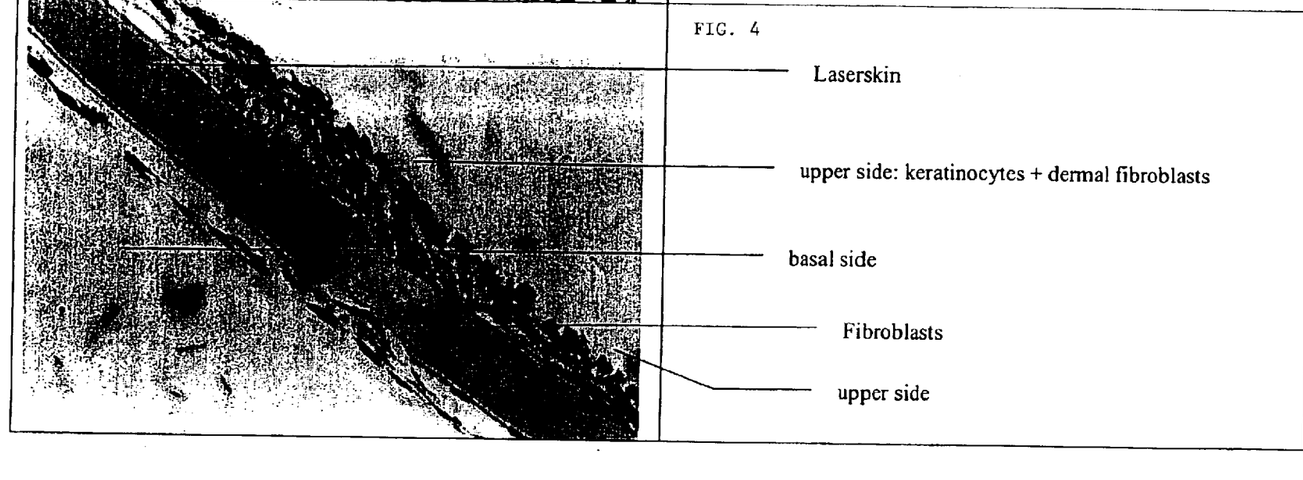
FIG. 4 is a photograph at 400× magnification depicting a Type A modified Composite Biocompatible Skin Graft (CBSG) according to the invention wherein allogenic fibroblasts were seeded on both sides of the LASERSKIN™ artificial skin.
Figure 5:
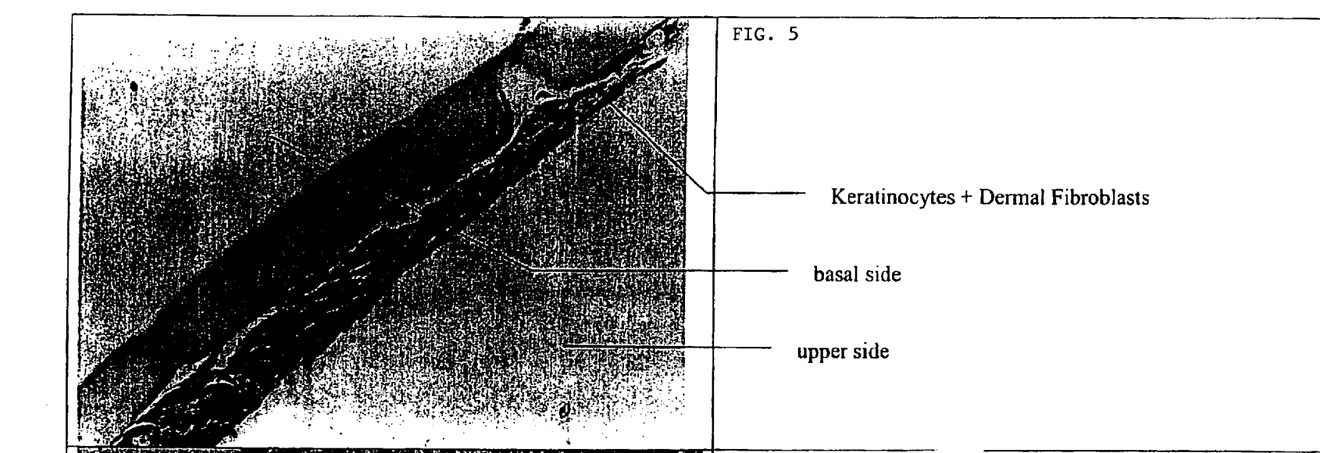
FIG. 5 is a photograph at 400× magnification depicting Type B modified Composite Biocompatible Skin Graft (CBSG) according to the invention wherein fibroblast was seeded on the side opposite the basal side of the LASERSKIN™ artificial skin.
Figure 6:
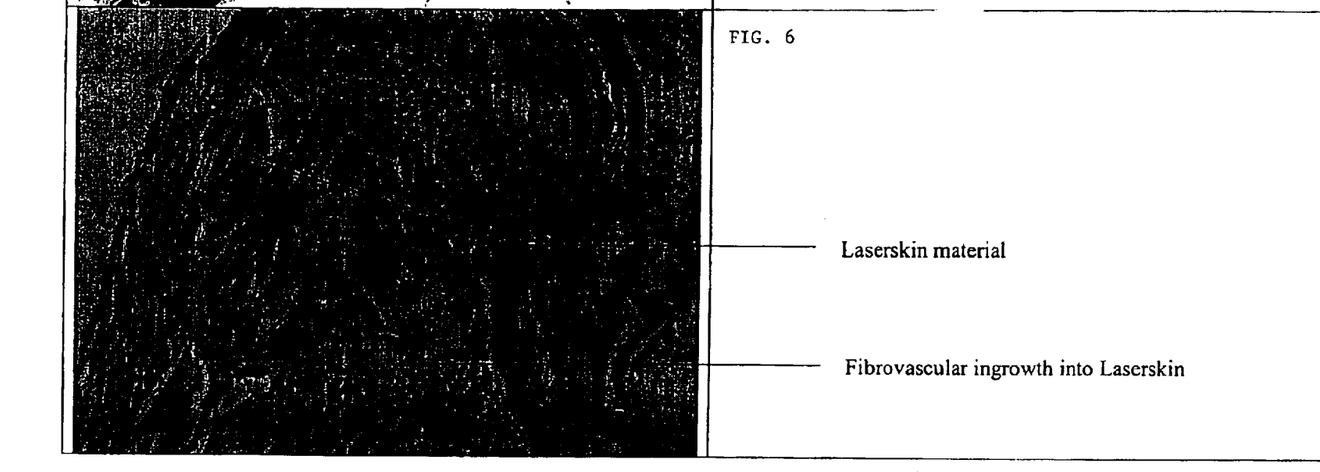
FIG. 6 is a photograph at 300× magnification depicting a complete epithelization of rat wounds grafted with Type A CBSG.
Figure 7:
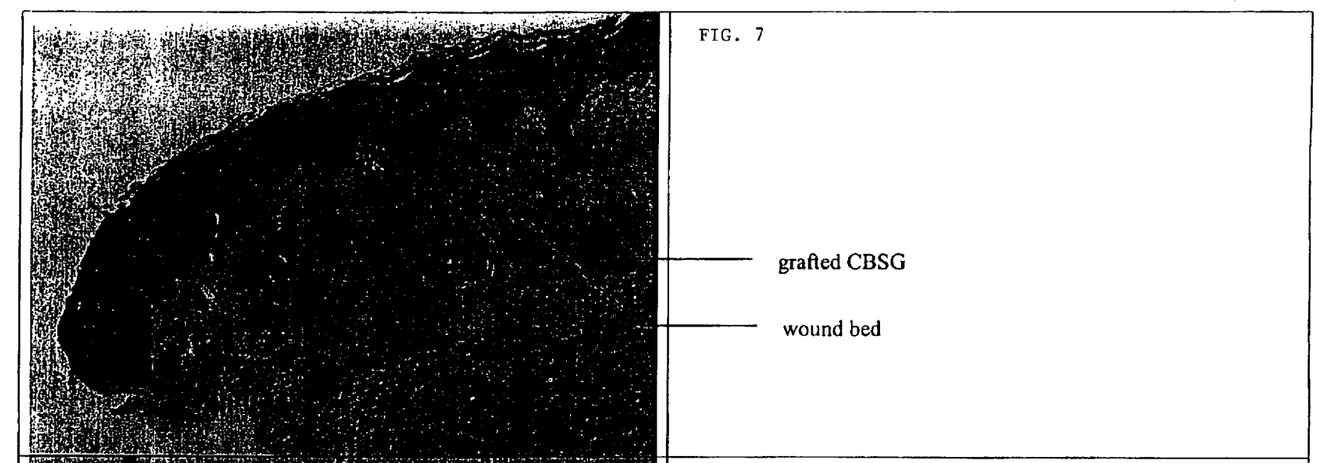
FIG. 7 is a photograph at 100× magnification depicting a complete epithelization of rat wounds grafted with type A CBSG.
Figure 8:
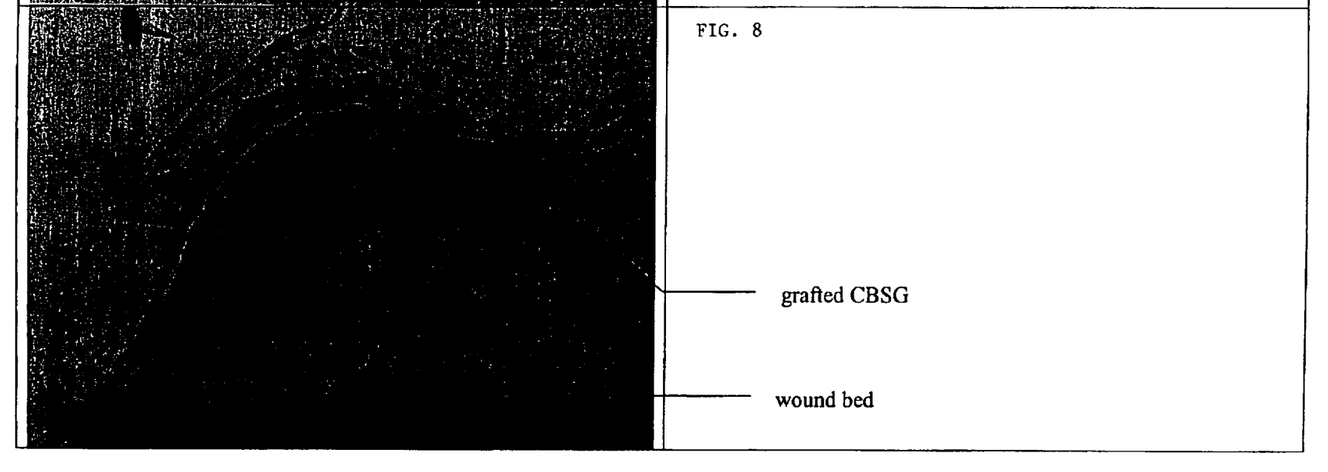
FIG. 8 is a photograph at 100× magnification depicting a complete epithelization of clinical wounds grafted with type B.

FIG. 2A is an illustration of a first stage in an engraftment method according to the invention. In FIG. 2A there is a wound bed 26 of a patient on Day Zero prior to the commencement of treatment. An artificial skin substrate 20 is applied upon the wound bed 26. The artificial skin substrate 20 has a basal side and an upper side. It comprises a layer 24 of collagen-glycoaminoglycan on its basal side, thus in a position to be juxtaposed to the wound bed 26. A covering membrane 22 of silicone is on the opposing upper side of the substrate 20. For a period of about fourteen days to about twenty-one days, the wound bed remains covered in order to allow vascularization of the neodermis. Referring to FIG. 2B, at this point, the silicone membrane 22 is removed from the vascularized neodermis of artificial skin 24' in preparation for immediate further treatment. Referring to FIG. 2C, one of Type A, B or C composite skin graft material 28 is engrafted on the layer 24'. In the specific embodiment, the material 28 comprises a substratum 34 having thereon autologous cultivated keratinocytes 30 of the donor patient, typically having thereunder on the substratum a layer of dermal fibroblasts 32, depending on the type of graft material 28.

The following is a detailed discussion of the materials and results of actual clinical experiments.

LASERSKIN™ Artificial Skin

LASERSKIN™ artificial skin is a biosynthetic biocompatible substratum for keratinocyte cultivation according to the invention. It is a form of thin and pliable biosynthetic membrane comprising a 100% benzyl esterified hyaluronic acid derivative. LASERSKIN™ artificial skin is commercially available from Fidia Advanced Biopolymers Ltd., Abano Terme (PD), Italy. LASERSKIN™ artificial skin was found to be useful to the inventors' experiments, although its preparation and application are not done according to the manufacturer's conventional instructions. There is nothing to preclude the use of compatible bioequivalents or human skin substitutes would also work in a similar fashion with the inventive CBSG.

Keratinocyte and Fibroblast Culture Sources

In the specific experiments undertaken, human keratinocytes and fibroblasts were derived from human foreskin obtained from circumcision for the human part of study. Rat keratinocytes and fibroblasts were obtained from Spraque Dawley rat (body weight, 400–450 gm). The primary cultures of human and rat keratinocytes were grown on mitomycin C-treated 3T3 feeder layer. The secondary and tertiary cultures of human keratinocytes were maintained in defined keratinocyte growth medium (Gibco), whereas rat keratinocytes were continuously grown on 3T3 feeder layer. Fibroblasts were cultivated in DMEM supplemented with 10% FBS.

Comparison of Seeding Efficacy of Human Keratinocytes on LASERSKIN™ Artificial Skin Human dermal fibroblasts and 3T3 cells were grown separately on LASERSKIN™ artificial skin with DMEM supplemented with 10% FBS. At sub-confluency, the 3T3 cells were treated with mitomycin-C (4 mg/ml) for 2 hours at 37° C., whereas the human fibroblasts were not treated. Human keratinocytes were seeded ($3\times10^4$ cells/cm$^2$) on top of the LASERSKIN™ artificial skin either pre-seeded with 3T3 cells or human fibroblasts. The keratinocyte suspension was instilled and concentrated on the Laserskin surface (0.5 ml/cm$^2$). Thirty minutes after seeding, DMEM supplemented with 10% FBS, insulin (4 mg/ml), cholera toxin (6 ng/ml), and EGF (10 ng/ml) (per Rheinwald et al. 75) were added to the culture.

In a control run, human keratinocytes were also seeded on top of plain LASERSKIN™ artificial skin (FIG. 1C). Efficacy was exhibited as hereinafter noted. After incubation at 37° C. in a humidified atmosphere with 5% $CO_2$ for 24 hours, the non-seeded keratinocytes on the LASERSKIN™ artificial skin were gently rinsed off with PBS. The cells were then counted with a hemocytometer. In order to quantify the number of fibroblasts or 3T3 cells detached together with the non-seeded keratinocytes during the washing of the LASERSKIN™ artificial skin, the LASERSKIN™ artificial skin without keratinocytes but seeded with equivalent number of 3T3 cells or fibroblasts were included as control.

Comparison of Seeding Efficacy of Rat Keratinocytes on LASERSKIN™ Artificial Skin The seeding of rat keratinocytes on LASERSKIN™ artificial skin was performed according to a technique essentially the same as the seeding of human keratinocytes. Rat fibroblasts were used to replace the human fibroblasts.

Preparation of CBSG Graft for Use on Full-thickness Wounds

Three different types of composite skin graft (CBSG) materials were compared and tested in animals, specifically laboratory rats. Type A CBSG consisted of allogenic rat fibroblasts seeded onto the basal side of a LASERSKIN™ artificial skin substratum. The fibroblasts were stimulated to produce collagen and other proteins by feeding the fibroblasts with DMEM supplemented with 10% FBS and 50 $\mu$m ascorbic acid. After ten days, the LASERSKIN™ artificial skin substratum was turned over and the upper side was seeded with fibroblasts. The fibroblasts on both sides were then fed with DMEM supplemented with 10% FBS. When the fibroblasts on the upper side became sub-confluent, rat keratinocytes were seeded ($3\times10^4$ cells/cm$^2$) on top of the upper surface of CBSG material. The cells were fed with DMEM supplemented with 10% FBS, insulin (4 mg/ml), cholera toxin (6 ng/ml), EGF(10 ng/ml). The keratinocytes became sub-confluent and were ready for grafting after only four to six days.

Two further types of CBSG materials were prepared. In Type B CBSG materials, the fibroblasts and keratinocytes were grown only on the upper side of the substratum. In Type C CBSG, keratinocytes alone were seeded on the upper side. As will be evident hereafter, all three types had a demonstrable efficacy.

Grafting Procedures:

Using twenty Spraque Dawley rats for the experiment, three separate full-thickness wounds, 2 cm in diameter each, were created on the dorsal area of each animal. The CBSG sheets were rinsed thoroughly with sterile PBS in a culture dish. They were lifted from the culture dish and placed directly on the wound so that the basal side of the CBSG was in contact with the wound. Non-adherent dressing was placed over the graft site. Each animal was engrafted with the three different types of CBSG materials. The migration of the epithelium from the cut wound edge was prevented by application of a polypropylene ring. The entire dressing was protected with porous thermal plastic. All grafts consisted of autologous keratinocytes and allogenic dermal fibroblasts.

Data Analysis:

The 'take' rate of the CBSG materials was analyzed with the Fisher Exact Test using Stat Xact (version 2.05). In multiple comparisons, the p values were further adjusted by the Bonferron method (i.e., multiplying the p value obtained from each test by k paired comparisons) in order to account for the so called 'serial t test'.

Results

Twenty-four hours after the seeding on the CBSG substratum, the non-viable and unseeded keratinocytes were carefully washed away and concentrated for counting. There were no detectable 3T3 cells or fibroblasts detached from the LASERSKIN™ artificial skin during the washing procedure. The seeding efficacy of keratinocytes was calculated as:

Total keratinocytes count (before seeding)–non-seeded keratinocytes Total keratinocytes count (before seeding)×100%

It is evident that the selected type of CBSG substratum provided a suitable culture template for the in vitro proliferation of keratinocytes. On a plain LASERSKIN™ artificial skin substratum, human keratinocytes showed a mean seeding efficacy of 75%. These human keratinocytes had a 95% seeding efficacy on LASERSKIN™ artificial skin populated with human fibroblasts and a 98% on 3T3 cell-seeded LASERSKIN™ artificial skin (Table 1). Rat keratinocytes had a seeding efficacy of 36% on plain LASERSKIN™ artificial skin. The respective seeding efficacies of rat keratinocytes on 3T3 LASERSKIN™ artificial skin and on allogenic fibroblasts/LASERSKIN™ artificial skin were 91% and 88%. The seeding efficacies of human/rat keratinocytes growing on 3T3 cell/LASERSKIN™ artificial skin or on allogenic fibroblasts/LASERSKIN™ artificial skin were significantly (p <0.001) better than those seeded on plain LASERSKIN™ artificial skin, as noted in the Fisher Exact Testing using Stat Xact (version 2.05) statistical package.

It is believed that human/rat fibroblasts could achieve a role similar to that of the 3T3 cells in enhancing the seeding efficacies of keratinocytes growing on LASERSKIN™ artificial skin with respective p values of 0.445 and 0.646 using the same statistical package.

The optical transparency of the LASERSKIN™ artificial skin allowed regular inspection of the grafted wound bed as it healed. Skin biopsies were taken from the center of the grafted area of the subject. It was observed that the polypropylene ring prevented the migration of epithelium from the wound edge as no epithelial cell was found in the control rat wound sutured with polypropylene ring alone up to day 21. In sixteen out of the twenty (80%) animal wounds covered with Type A CBSG, the keratinocytes formed a multilayered epithelium that had a basal layer in contact with underlying connective tissue. The undersurface of epidermis did not show rete. Fibrovascular ingrowth of connective tissue into the LASERSKIN™ artificial skin was observed. Eight (40%) of the Type B CBSG sites and seven (35%) of the Type C CBSG sites showed re-epithelization. Histologically there was no observable epithelium in 3 (15%), 10 (50%), and 12 (55%) of the grafted CBSG sites of Types A, B and C respectively (Table 2).

The graft take rate of Type A CBSG was found to be significantly higher than those of Types B and C CBSG in the Fisher Exact Test/Bonferron method analysis with respective p values of 0.0419 and 0.018. There was no significant difference (p>0.1) of the graft take rate between Types B and C CBSG(table 2). Infection occurred in only one (5%) animal with a Type A or C CBSG graft and in two (10%) animals with a Type B CBSG graft.

A preliminary clinical trial of CBSG was also conducted on two human burn patients (designated CLB & CKT). Three out of the five (60%) grafted wounds in patient CLB developed stratified epithelium (Table 3). The other two grafts were lost because of the bacterial colonization at the adjacent tissues. All three skin biopsies from patient CKT showed complete epithelization with primitive rete ridge formation. There was no severe immunologic reaction to the allogenic fibroblasts in these two patients or in the animal experiments. Clinically, the CBSG grafts were durable. All grafts were histologically confirmed as a 'tak' at two weeks, and they remained clinically intact on the recipient wound at eight weeks post-grafting. No further biopsies were taken of the patients.

Discussion

Problems encountered in cultivation of keratinocytes on LASERSKIN™ artificial skin can be attributed to limited experience on this new product. Hyaluronic acid is a mucopolysaccharide with alternating β1–3 glucuronidic and β1–4 glycosaminidic bonds. LASERSKIN™ artificial skin mainly consists of 100% benzyl esterified hyaluronic acid. A weak electrostatic association exists between the keratinocytes and the LASERSKIN™ artificial skin. Since the volume and surface area of human keratinocytes differ from those of rat keratinocytes, there is a variation of charge density of two cell populations. Consequently they have different seeding efficacies on plain LASERSKIN™ artificial skin. The species-specific difference was abolished by cultivating keratinocytes on 3T3 cell/LASERSKIN™ artificial skin because 3T3 cells were the dominant factors influencing keratinocyte attachment on LASERSKIN™ artificial skin.

The seeding efficacies of human and rat keratinocytes ($3 \times 10^4$ cells/cm$^2$) were 75% and 36% respectively on plain LASERSKIN™ artificial skin. The manufacturer of LASERSKIN™ artificial skin recommends seeding the human keratinocytes on the skin membrane pre-seeded with irradiated 3T3 cells. Good seeding efficiencies of 98% (human keratinocytes) and 91% (rat keratinocytes) were demonstrated on LASERSKIN™ for artificial skin with Mitomycin-treated 3T3 cells. In Green's method, keratinocytes are seeded on a 3T3 cell feeder layer which allows a rather low seeding density of $6–10 \times 10^4$ cells/cm$^2$ for the primary culture. A smaller seeding density of $2–5 \times 10^4$ cells/cm$^2$ is feasible for the secondary and tertiary cultures. The utility of cultured epidermal autograft grown on culture dish using Green's feeder layer technique is limited by the persistent 3T3 fibroblasts which sensitize the host to xenogenic antigen resulting in late graft rejection. The 3T3 cells were found less likely to be washed away from the LASERSKIN™ artificial skin material. However, allogenic fibroblasts can achieve a similar role as 3T3 cells in initiation of keratinocyte colonization on LASERSKIN™ artificial skin.

It is evident that the CBSG material consisting of cultured keratinocytes and dermal fibroblasts is a good human skin substitute for freshly excised full-thickness wounds which were previously grafted with allografts.

TABLE 1

Mean Seeding Efficacies of Human and Rat Keratinocytes on LASERSKIN™ artificial skin. 15 determinations were made. Seeding efficacies of human/rat keratinocytes were significantly improved by 3T3 cells/fibroblasts ($p < 0.001$).

| LASERSKIN™ Artificial Skin Preparation | Human Keratinocytes | Rat keratinocytes |
| --- | --- | --- |
| Plain | 75% | 36% |
| with 3T3 cells | 98% | 91% |
| with human fibroblasts | 95% | — |
| with rat fibroblasts | — | 88% |

TABLE 2

Evaluation of Composite Biocompatible Skin Graft on Animals
Type A CBSG had a higher graft take rate than types B & C with respective p values of 0.0419 and 0.018.

| Results | Type A (N = 20) Keratinocytes + Fibroblasts on both sides | Type B (N = 20) Keratinocytes + Fibroblasts on upper side | Type C (N = 20) Keratinocytes alone |
| --- | --- | --- | --- |
| Grafted epithelium observed | 16(80%) | 8(40%) | 7(35%) |
| No epithelium observed | 3(15%) | 10(50%) | 12(55%) |
| Infection | 1(5%) | 2(10%) | 1(5%) |

TABLE 3

Preliminary Clinical Trials on Composite Biocompatible Skin Graft.
'v' = 'take'; 'X' = 'not take'

| | Grafted sites | Graft Histology |
| --- | --- | --- |
| Patient CLB | Left hand (2) | v v |
| | Left arm | X |
| | Left forearm | v |
| | Left shoulder | X |
| Patient CKT | Left arm | v |
| | Left forearm (2) | v v |

Attempts were made to graft freshly harvested epidermis onto INTEGRA™ neodermis in animal experiments. The dermal-epidermal separation was performed with dispase. The epidermal graft was not easily 'taken' by the neodermis whereas thin split thickness autografts readily incorporated on the neodermis as in many clinical applications. It is believed that the presence of fibroblasts in the dermis of the thin autograft may play an essential role in the keratinocyte attachment and its proliferation on the neodermis. It was observed that, during wound healing, cell-cell interactions between epidermal keratinocytes and dermal fibroblasts contributed to the organization of epidermis. Prostaglandin E2 (PGF2) is considered to be involved in the proliferation and differentiation of keratinocytes. The production of PEG2 was enhanced in the co-culture of keratinocytes and fibroblasts, whereas the PEG2 production was negligible in monolayer cultures of keratinocytes or fibroblasts. The fibroblasts also produced two soluble heparin-binding growth factors such as keratinocyte growth factor and hepatocyte growth factor/scatter factor that promote DNA synthesis and proliferation of keratinocytes.

The combination of the inventive CBSG material including keratinocytes and dermal fibroblasts and INTEGRA™ artificial skin material was applied to a 28-year old man with extensive hypertrophic burn scars and neck contracture. Multiple wounds from scar excision with a total area of approximately 250 $cm^2$ were covered with INTEGRA™ artificial skin material. At the same time a skin biopsy was taken for keratinocyte culture. Two weeks later, the top silicone layer of the artificial skin was removed. The neodermis of the artificial skin was then covered with the CBSG. At Days 6 and 14 after the application of CBSG, biopsies were taken from center of one of the wounds. The histology at Day 6 showed early epithelization with a few squamous epithelial cells settling on top of the scaffolds of the INTEGRA™ artificial skin material and the LASER-SKIN™ artificial skin material. Most of the epithelium were single-layer flattened squamous cells. The biopsy taken on Day 14 showed a viable 2- to 4-cell-thick squamous epithelium with minimal inflammation. The wounds were completely epithelized within four weeks of the application of the CBSG. Biopsies taken from other wounds showed similar findings.

The invention has now been explained with reference to specific embodiments. Other embodiments will be evident to those of ordinary skill in the art. It is therefor not intended that this invention be limited, except as indicated by the appended claims.

What is claimed is:

1. A method for cultivating a skin material for grafting onto a neodermis of a human patient, comprising:

growing a first layer of human dermal fibroblasts upon a basal side of a biosynthetic substratum of an esterified hyaluronic acid;

growing a second human dermal fibroblast layer upon an upper side of said biosynthetic substratum; and after said second dermal fibroblast layer begins to proliferate, growing a layer of keratinocytes over said second layer to form a composite skin material, said keratinocytes having been harvested from said patient.

2. The method according to claim 1 wherein said dermal fibroblasts are allogenic to the keratinocytes.

3. The method according to claim 1 wherein said dermal fibroblasts are autologous to the keratinocytes.

4. A skin material for grafting onto a neodermis of a human patient, said material comprising a composite of:

a biosynthetic substratum of an esterified hyaluronic acid;

a layer of viable human dermal fibroblasts upon an upper side of said biosynthetic substratum; and a layer of viable human keratinocytes over said dermal fibroblasts upon said upper side of said substratum, said keratinocytes having been harvested from said patient.

5. The material according to claim 4 wherein said dermal fibroblasts are allogenic to the keratinocytes.

6. The material according to claim 4 wherein said dermal fibroblasts are autologous to the keratinocytes.

7. A skin material for grafting onto a neodermis of a human patient, said material comprising a composite of:
- a biosynthetic substratum of an esterified hyaluronic acid;
- a first layer of viable human dermal fibroblasts upon a basal side of said biosynthetic substratum;
- a second layer of viable human dermal fibroblasts upon an upper side of said biosynthetic substratum; and
- a layer of viable human keratinocytes over said dermal fibroblasts upon said upper side of said substratum, said keratinocytes having been harvested from said patient.

8. The material according to claim 7 wherein said dermal fibroblasts are allogenic to the keratinocytes.

9. The material according to claim 7 wherein said dermal fibroblasts are autologous to the keratinocytes.

10. A method for grafting a cultivated skin material onto a human patient, comprising the steps of:
- applying an artificial skin substrate upon a wound bed of said patient; said artificial skin substrate comprising a layer of collagen-glycoaminoglycan on a basal side to be juxtaposed to said wound bed and a covering membrane of silicone on an opposing upper side;
- allowing a vascularized wound bed to form under said collagen-glycoaminoglycan; thereupon
- removing said silicone membrane; and
- applying a basal side of a sheet of the cultivated skin material over said collagen-glycoaminoglycan, said cultivated skin material comprising a layer of keratinocytes overlying a layer of viable human dermal fibroblasts upon an upper side of a biosynthetic substratum, said keratinocytes being harvested from said patient.

11. The method according to claim 10 wherein said cultivated skin material further comprises a layer of dermal fibroblasts upon said basal side of said biosynthetic substratum.

12. A method according to claim 10, wherein said biosynthetic substratum is a substratum of an esterified hyaluronic acid.

13. The method according to claim 12 wherein said cultivated skin material further comprises a layer of dermal fibroblasts upon said basal side of said biosynthetic substratum.

14. The method of claim 1, wherein the esterified hyaluronic acid is benzyl esterified hyaluronic acid.

15. The material of claim 4, wherein the substratum is a membrane comprising benzyl esterified hyaluronic acid.

16. The material of claim 7, wherein the substratum is a membrane comprising benzyl esterified hyaluronic acid.

17. The method of claim 12, wherein the substratum is a membrane comprising benzyl esterified hyaluronic acid.

18. The method of claim 14, wherein the membrane has holes capable of draining exudate.

19. The material of claim 15, wherein the membrane has holes capable of draining exudate.

20. The material of claim 16, wherein the membrane has holes capable of draining exudate.

21. The method of claim 17, wherein the membrane has holes capable of draining exudate.

22. A method for grafting a cultivated skin material onto the wound bed of a human patient, comprising the steps of;
- covering the wound bed with a neodermis, and
- applying the cultivated skin material onto the neodermis; said cultivated skin material comprising a basal side and an upper side of a biosynthetic substratum and a layer of keratinocytes overlying a layer of viable human dermal fibroblasts upon said upperside, said keratinocytes being harvested from said patient.

23. The method of claim 22, wherein said fibroblasts are autologous to the Keratinocytes.

24. The method of claim 22, wherein said cultivated skin material further comprises layer of dermal fibroblasts upon said basal side of said biosynthetic substratum.

* * * * *